US010987285B2

(12) United States Patent
Misner et al.

(10) Patent No.: US 10,987,285 B2
(45) Date of Patent: Apr. 27, 2021

(54) METHOD OF RECLAIMING FORMULA COMPONENTS OF ANTIPERSPIRANT COMPOSITIONS

(71) Applicant: Colgate-Palmolive Company, New York, NY (US)

(72) Inventors: Steven Misner, Verona, NJ (US); Pablo Molina, Morristown, NJ (US); Richard Blume, Wind Gap, PA (US); Ronald Growe, Jr., Flanders, NJ (US); Frederick Eckert, Knoxville, TN (US); Peter Wisniewski, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/531,966

(22) PCT Filed: Dec. 4, 2014

(86) PCT No.: PCT/US2014/068525
§ 371 (c)(1),
(2) Date: May 31, 2017

(87) PCT Pub. No.: WO2016/089403
PCT Pub. Date: Jun. 9, 2016

(65) Prior Publication Data
US 2017/0340525 A1 Nov. 30, 2017

(51) Int. Cl.
*A61K 8/02* (2006.01)
*A61Q 15/00* (2006.01)

(52) U.S. Cl.
CPC .......... *A61K 8/0229* (2013.01); *A61K 8/0216* (2013.01); *A61Q 15/00* (2013.01)

(58) Field of Classification Search
None
See application file for complete search history.

(56) References Cited

U.S. PATENT DOCUMENTS

| 2,566,359 | A | * | 9/1951 | Owen | C11D 13/04 516/75 |
| 3,793,215 | A | * | 2/1974 | Smith | C11D 1/123 510/154 |
| 5,429,747 | A | * | 7/1995 | Carr | C02F 1/283 210/650 |
| 5,990,074 | A | * | 11/1999 | Gross | C11D 13/00 510/141 |
| 2007/0253922 | A1 | | 11/2007 | Akitsu | |
| 2011/0076309 | A1 | * | 3/2011 | Misner | A61K 8/0229 424/401 |

FOREIGN PATENT DOCUMENTS

| CN | 101061997 | 10/2007 |
| CN | 101240226 | 8/2008 |
| CN | 103965940 | 8/2014 |
| RU | 2106365 C1 | 3/1998 |
| SU | 1745759 | 7/1992 |
| WO | 2012/006400 | 1/2012 |

OTHER PUBLICATIONS

Kirk-Othmer Encyclopedia of Chemical Technology, Polyaluminum, Chlorides, pp. 1-7. (Year: 2000).*
Soap and Detergent Manufacture, pp. 1-12. (Year: 1988).*
Bardelline, Tom's New Deodorant Packaging Is Fully Recyclable (Where Accepted), Greenbiz. (Year: 2009).*
Neuffer, EPA-450/3-88-002, Sodium Hydroxide Preliminary Source Assessment, U.S. Environmental Protection Agency. (Year: 1988).*
International Search Report and Written Opinion in International Application No. PCT/US2014/068525, dated Aug. 6, 2015.
Zeng Yikun, Oleochemical Industry, China Business Press, pp. 54-59, published on Feb. 29, 1996.

* cited by examiner

*Primary Examiner* — Melissa S Mercier

(57) ABSTRACT

Methods for reclaiming formula components of an antiperspirant composition and recycling formula into its component parts for recycling into an antiperspirant composition.

18 Claims, No Drawings

METHOD OF RECLAIMING FORMULA COMPONENTS OF ANTIPERSPIRANT COMPOSITIONS

BACKGROUND

Production of consumer care products such as antiperspirant/deodorant products occurs on a large scale and can generate scrap material. This can negatively impact product cost as well as sustainability positioning. Thus, there is a need to develop processes for reclaiming scrap materials to reduce cost and environmental impact.

BRIEF SUMMARY

Methods for reclaiming and reusing formula components from scrap antiperspirant/deodorant compositions are described in the present disclosure. According to one embodiment, the methods include melting a solid or semi-solid antiperspirant composition; settling the antiperspirant composition into a solid phase, and a liquid phase having an oil/wax phase; separating the solid phase from the oil/wax phase; and, treating the liquid phase to reclaim one or more components thereof. According to another embodiment, methods of forming soap from scrap antiperspirant compositions include separating an oil/wax phase of a molten solid or semi-solid antiperspirant composition; saponifying the oil/wax phase to form a saponified soap mass; fitting the saponified soap mass to form a fitted soap mass; and separating a neat soap from the fitted soap mass.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Antiperspirant compositions according to the present disclosure can include a plant oil, an emollient, a gellant, an antiperspirant active and, optionally, a deodorant active. In one embodiment, the composition is a solid stick or semi-solid when at ambient room temperature of about 25° C. The stick form is an example of a solid form, and the semi-solid is a thickened form that may or may not be solid. The stick form can be distinguished from a semi-solid in that, in a stick, the formulated product can retain its shape for extended time periods outside the package, the product not losing its shape significantly (allowing for some shrinkage due to solvent evaporation). Adjustment of amounts of gelling or thickening agents can be used in order to form a semi-solid or stick The antiperspirant compositions including a plant oil can include blends or mixtures of plant oil. By plant oil it is meant that the oil is obtained from a plant, or the plant oil can be made by blending of oil components to obtain an oil that is substantially similar in composition to a plant oil. By substantially similar, it is meant that the manufactured oil contains at least 50 weight % (or at least 60, 70, 80, 90, 95, 98, or 99 weight %) of the components that are found in the plant oil that it is designed to mimic. In certain embodiments, the plant oil has a melting point below 40° C. or below 35° C. or below 30° C.

Examples of the plant oil include, but are not limited to, palm kernel, coconut, avocado, canola, corn, cottonseed, olive, palm, hi-oleic sunflower, mid-oleic sunflower, sunflower, palm stearin, palm kernel olein, safflower, and babassu oils. In one embodiment, palm kernel oil is the selected oil. In another embodiment, coconut oil is the selected oil. In another embodiment, the plant oil is a combination of palm kernel oil and coconut oil.

Gellants are those materials known in the art that can structure the antiperspirant compositions. Examples include, but are not limited to waxes, fatty alcohols, hydrogenated vegetable oils, hydrocarbon waxes, esters of fatty acid and fatty alcohol, triglycerides, or other cosmetically acceptable materials, which are solid or semi-solid at room temperature and provide a consistency suitable for application to the skin.

In one embodiment, the hydrogenated oil is hydrogenated soybean oil. In one embodiment, the hydrogenated soybean oil is almost, but not fully hydrogenated. The amount of hydrogenation is measured by the iodine value. The iodine value can be measured by ASTM D5554-95 (2006). In one embodiment, the iodine value of the hydrogenated soybean oil used herein is greater than 0 to 20. In one embodiment, the iodine value is 1 to 5. In another embodiment, the soybean oil is fully hydrogenated with an iodine value of 0. In another embodiment, the iodine value is up to 20. In one embodiment, the gellant includes a partially hydrogenated soybean oil having an iodine value in the range of about 75 to about 80.

The hydrocarbon wax can be a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene. In one embodiment, the hydrocarbon is synthetically made from methylene to form a polymethylene.

The fatty alcohol can be any fatty alcohol. In one embodiment, the fatty alcohol is stearyl alcohol or behenyl alcohol or a mixture of both.

In another embodiment, the gellant includes hydrogenated castor oil (castor wax). In certain embodiments, the melting point of the castor wax is 70 to 90, or it can be 70, 80, or 90.

In one embodiment, the gellant is a combination of the hydrogenated soybean oil with a fatty alcohol, and castor wax.

The antiperspirant compositions can contain emollients in any desired amount to achieve a desired emollient effect. Emollients are known in the art and are used to impart a soothing effect on the skin. One class of emollients is non-volatile emollients and can include non-silicone and silicone emollients. Examples of non-volatile, non-silicone emollients include, but are not limited to, $C_{12-15}$ alkyl benzoate, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, cetyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminoglucon-ate, vegetable oils, isodecyl oleate, isostearyl neopentanoate, myristyl myristate, oleyl ethoxy myristate, diglycol stearate, ethylene glycol monostearate, myristyl stearate, isopropyl linolate, paraffin waxes, glycyrrhizic acid, hydrocyethyl stearate amide. The non-volatile silicone material can be a polyethersiloxane, polyalkyarylsiloxane or polyethersiloxane copolymer.

Antiperspirant actives, according to the present disclosure, include any of the known antiperspirant active materials. Antiperspirant actives include, but are not limited to aluminum chlorhydrate, aluminum chloride, aluminum sesquichlorohydrate, aluminum-zirconium hydroxychlorides, and complexes or adducts of the above-mentioned active ingredients with glycol, such as propylene glycol and combinations thereof. Known aluminum-zirconium salts in combination with neutral amino acids, such as glycine (e.g., aluminum-zirconium tetrachlorohydrex Gly) can also be used. Generally, any of the Category 1 active antiperspirant ingredients, listed in the Food and Drug Administration's Monograph on Antiperspirant Drug Products for overall-the-counter human use (Oct. 10, 1973) can be used.

In other embodiments, the antiperspirant active is an aluminum salt and/or an aluminum-zirconium salt, such as those described above, that are further stabilized by betaine and a calcium salt. In other embodiments, the antiperspirant active, such as those described above, is selected to have a low metal to chloride ratio. In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to the following: astringent salt of aluminum, astringent salt of zirconium, aluminum bromohydrate, aluminum chlorohydrate, aluminum dichlorohydrate, aluminum sesquichlorohydrate, aluminum chlorhydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats.

According to one embodiment, the antiperspirant compositions are a solid in stick form and include palm kernel oil, $C_{12-15}$ alkyl benzoate, PPG-14 butyl ether, castor wax, behenyl alcohol, stearyl alcohol, hydrogenated soybean oil, an antiperspirant active, and optionally, one or more solid or particulate additives and/or a deodorant active.

According to the present disclosure, methods for reclaiming and reusing formula components from scrap antiperspirant/deodorant compositions are described. According to one embodiment, the methods include melting a solid or semi-solid antiperspirant composition; settling the antiperspirant composition into a liquid phase having an oil/wax phase, and a solid phase; separating the solid phase from the oil/wax phase; and treating the liquid phase to reclaim one or more components thereof.

According to methods described in the present disclosure, scrap antiperspirant materials (either in solid or semi-solid form) are collected for melting to cause the separation of the composition into a solid phase and a liquid phase. The solid phase will typically include the antiperspirant active, along with other solid particulate matter, and is most often inorganic in composition. According to one embodiment, the solid phase can constitute 10 percent to 30 percent by weight of the antiperspirant composition, for example, 20 percent by weight of the composition.

The melting step, according to one embodiment, includes heating the antiperspirant compositions to a desired temperature or range of temperatures sufficient to melt a desired formula component or components into the liquid phase. According to one embodiment, melting the composition includes heating the composition at a temperature in a range of 70° C. to 100° C., for example, heating the composition at a temperature in a range of 80° C. to 90° C. In a preferred embodiment, the composition is heated to a temperature of 85° C. Heating can be performed by any method known in the art. According to one embodiment, the composition can be heated in an oven. According to another embodiment the composition can be heated in a water bath. Vessels suitable for containing the antiperspirant compositions during heating can include, for example, glass, plastic, metals such as stainless steel, or ceramic containers. Further, the vessels can have a volume corresponding to an appropriate size for containing a desired amount of antiperspirant scrap. For example, vessel volumes can range from as small as 1 liter beakers, up to, and including 100 gallon batch vessels or larger, depending on batch size for separation. It should be appreciated that the composition can be melted at any temperature and in any manner as desired such that the antiperspirant composition formula components are distributed into their respective desired solid or liquid phases.

According to one embodiment, the scrap antiperspirant compositions are disposed within a package including recyclable material, for example, a recyclable plastic. In such embodiments, the method can further include the step of removing the antiperspirant composition from the package and recycling the recyclable material of the package. According to one embodiment, the step of removing the antiperspirant composition from the package can occur after the step of melting the composition. In an alternative embodiment, the scrap antiperspirant composition can be removed from the package prior to the step of melting. The step of recycling the recyclable material can occur at any time as desired after the composition has been removed from the package. In certain embodiments, a washing step can be included to remove any residue antiperspirant composition from the package prior to recycling the recyclable material.

The step of settling the melted antiperspirant composition, according to the present disclosure, settles the melted composition into a liquid phase having an oil/wax phase, and a solid phase. According to one embodiment, the liquid phase can further include an aqueous component. In a preferred embodiment, the liquid phase includes a plant oil, a fatty alcohol, and an emollient. An exemplary liquid phase can include palm kernel oil, $C_{12-15}$ alkyl benzoate, PPG-14 butyl ether, castor wax, behenyl alcohol, stearyl alcohol, and hydrogenated soybean oil.

The time for the settling step can vary to achieve a desired level of settling between the liquid phase and the solid phase and can be as long as 72 hours. According to one embodiment, the settling for the melted antiperspirant composition can occur within a time period of less than 6 hours, or can occur in the range of 6 hours to 36 hours, for example, within a time period in the range of 12 hours to 24 hours.

According to one embodiment, the step of separating the oil/wax phase and the solid occurs after the step of settling. Separating the oil/wax phase from the solid phase can be done in any manner as desired. In one embodiment, the step of separating is done by decanting the oil/wax phase from the solid phase.

According to another embodiment, the step of separating can include the step of washing the liquid phase. The step of washing according to one embodiment can include contacting the liquid phase with water and mixing (or otherwise agitating) to attempt to ensure no residual solid phase remains in the oil/wax phase. According to one embodiment, the water used in the washing step is at a temperature high enough to prevent re-solidifying any desired liquid phase formula components. Such a washing step can enhance the separation of the oil/wax phase from the solid phase (containing the antiperspirant active). The addition of hot water in combination with moderate to high agitation of the melted antiperspirant composition can allow for an effective separation of a heavier aqueous phase containing the antiperspirant active from the oil/wax phase containing the oil and wax components of the antiperspirant composition. This water washing step can potentially accelerate the separation of the oil/wax phase and solid phase and can also provide a more defined separation of these phases for downstream processing. The quantity of wash water used can vary from 5%-100% by weigh of the melted antiperspirant composition; preferably between 10% and 50% by weight; and more preferably 25% to 35% by weight. Processing temperatures for the washing step can be similar to those described for the melting and settling steps; e.g., 70° C. to 100° C. In one embodiment, the washing step separates the oil/wax phase and the solid phase within 3 hours. According to one embodiment, the washing step distributes the antiperspirant active in the aqueous phase.

According to one embodiment, the step of treating the liquid phase includes the removing the aqueous phase for reclaiming of the antiperspirant active. According to a further embodiment, the step of treating the liquid phase includes saponifying the oil/wax phase. In one embodiment, saponifying the oil/wax phase includes contacting with a caustic alkali solution. According to one embodiment, the oil/wax phase includes any triglyceride, fatty acid, fatty alcohol or wax that is suitable for an antiperspirant composition. In certain preferred embodiments, the oil/wax phase includes palm kernel oil, castorwax, behenyl alcohol, stearyl alcohol, and hydrogenated soybean oil. Treating the oil/wax phase by saponifying, in certain embodiments, includes reclaiming one or more components thereof. Such reclaimed components can be used, for example, as raw materials in different manufacturing processes for consumer products as well as being reusable process ingredients that can be utilized in the methods described herein in addition to different manufacturing processes for consumer products. According to one embodiment, the reclaimed component is a neat soap. According to a further embodiment, reclaimed component is a spent lye suitable for re-use in future saponification processes.

According to the present disclosure there are further described methods of forming a soap from scrap antiperspirant compositions. According to one embodiment, the methods are batch soap making processes. According to an alternative embodiment, the methods are continuous soap making processes. The methods include separating an oil/wax phase of a molten solid or semi-solid antiperspirant composition; saponifying the oil/wax phase to form a saponified soap mass; fitting the saponified soap mass to form a fitted soap mass; and, separating a neat soap from the fitted soap mass. The scrap antiperspirant compositions according to these methods are those that have been previously described. According to one embodiment, the antiperspirant compositions can include an antiperspirant active, a plant oil, an emollient, and a fatty alcohol.

According to one embodiment, separating the oil/wax phase from the antiperspirant composition can include melting the solid or semi-solid antiperspirant composition into a molten solid or semi-solid antiperspirant composition to form a solid phase and a liquid phase, wherein the liquid phase includes an oil/wax phase. The oil/wax phase can be removed from the remaining constituent components in any manner as desired, for example, by decanting. According to one embodiment, the oil/wax phase includes palm kernel oil, castor wax, behenyl alcohol, stearyl alcohol, and hydrogenated soybean oil.

According to one embodiment, saponifying the oil/wax phase forms a saponified soap mass. Saponifying can include heating the oil/wax phase to a desired temperature or range of temperatures. In one embodiment, heating the oil/wax phase is at a temperature in the range of 80° C. to 120° C., for example at a temperature in the range of 90° C. to 110° C. In one preferred embodiment the oil/wax phase is heated to a temperature in the range of 95° C. to 100° C., and in another preferred embodiment, the oil/wax phase is heated to a temperature in the range of 85° C. to 95° C.

Saponifying the oil/wax can further include contacting the oil/wax phase with a caustic alkali solution. Caustic alkali solutions suitable for use in the present disclosure can have an alkali concentration in the range of 0.5% by weight to 50% by weight. In one embodiment, caustic alkali solutions can include potassium and sodium based caustic solutions, as well as mixtures of the same. Typically, the use of sodium based caustic solutions, such as sodium hydroxide (i.e., lye) are directed to the production of solid soaps; whereas, the use of potassium based caustic solutions are directed to the production of liquid soaps. According to one embodiment the caustic alkali solution is a sodium hydroxide solution. In certain embodiments, the caustic alkali solutions can further include alkali salt, which, in certain instances, can assist in the conversion of oils and fats in to a carboxylate salt (i.e., soap). According to one embodiment, the caustic alkali solution includes sodium chloride. In one embodiment, the caustic alkali solution constitutes 0.1 to 3 or 3 percent by weight of sodium hydroxide and 10 to 21 or 16 percent by weight of sodium chloride. In certain embodiments, contacting the oil/wax phase with a caustic alkali solution includes continuous agitation of the oil/wax phase during contact with the caustic alkali solution.

According to one embodiment, the step of saponifying the oil/wax phase can occur over any range time or times sufficient to saponify the oil and fats in the oil/wax phase to form a saponified soap mass. According to one embodiment, saponifying the oil/wax can occur in a time period in the the range of 2 hours to 6 hours, for example in the range of 3 hours to 4 hours. In a preferred embodiment, saponifying includes heating the oil/wax phase a temperature in the range of 85° C. to 100° C., contacting the oil/wax phase with the caustic alkali solution constituting 0.1 to 3 or 3 percent by weight of sodium hydroxide and 10 to 21 or 16 percent by weight of sodium chloride, and includes continuous agitation of the oil/wax phase during contact with the caustic alkali solution. The saponifying step preferably occurs in a time period of 3 hours to 4 hours, where the contacting step occurs for the first 1 hour to 2 hours of saponifying the oil/wax phase.

According to one embodiment, after the step of saponifying, settling out of an aqueous alkali phase can occur in the saponified soap mass. The aqueous alkali phase can include a spent lye component and glycerol. Settling can occur for any duration and at any temperature as desired. For example, settling can occur in a time period of 1 hour to 2 hours at 85° C. According to a further embodiment, the saponified soap mass constitutes an aqueous alkali phase having a lye bulk in the range of 1.5 to 3, which can further enhance separation of the alkali and water soluble components from the saponified soap mass.

Following settling, according to one embodiment, the method can further include removing the aqueous alkali phase, which can include for example, the spent lye, glycerol, and other water soluble components. Further still, according to another embodiment, one or more of the components of the alkali aqueous phase can be further reprocessed or recycled for reuse in the saponification process or reclaimed for use as a component in a different production stream. For example, glycerol can be removed and recycled as a component for any number of commercial uses including multiple consumer products. Alternatively, a portion, up to and including all of the glycerol can remain in the saponified soap mass. Additionally, the spent lye can be processed for reuse in the saponification methods described herein.

Following removal of the alkali aqueous phase from the saponified soap mass, the method further includes fitting the saponified soap mass to form a fitted soap mass. Fitting is a process known in the art for refining soap masses. In certain embodiments, fitting includes diluting the saponified soap mass with an amount of water sufficient to separate the saponified soap mass into two phases including a soap slurry and a neat soap. According to additional embodiments, fitting includes treating the saponified soap mass with an additional caustic alkali solution in order to further refine the saponified mass. According to a further embodiment, fitting includes a settling step to increase separation between the slurry soap and the neat soap. In a preferred embodiment, settling of the fitted soap mass occurs for 48 hours to 72 hours.

Upon settling, separating the neat soap and the slurry soap can occur according to one embodiment. Upon separating, the method can include, according to another embodiment, processing the slurry soap for reuse in the saponification methods described herein. According to a further embodiment, the method can include drying of the neat soap to form soap chips for use as a component in other commercial processes including consumer care products. According to one embodiment, the neat soap can include an anhydrous soap, alkali salt, alkali hydroxide, glycerol, and water. For example, the neat soap can include an anhydrous soap, sodium chloride, sodium hydroxide, glycerol, and water. In a preferred embodiment, the neat soap can include 60% to 72% by weight of an anhydrous soap, 0.5% to 1.5% by weight of sodium chloride, 0.01% to 0.5% by weight of sodium hydroxide, 0.5% to 3% by weight of glycerol, with a remainder by weight of water.

EXAMPLES

Example 1

Batch Melt 4 kg of an antiperspirant composition contained within a plastic package was heated at 85° C. for 6-8 hrs until the composition was melted. The package material was taken out, washed to remove excess residue, and set aside for future recycling. The melted composition was transferred into a glass beaker at 85° C. for 72 hrs to allow the separation of the solid phase and oil/wax phase. Optionally, 1.3 kg of water can be added to wash the melted composition, and then the composition can be agitated for 2 hrs to assist in phase separation and the removal of residual solids from the oil/wax phase.

After separation is completed, the oil/wax phase and aqueous phase are measured volumetrically. The antiperspirant active is removed with the aqueous phase and set aside for re-use. The oil/wax phase is decanted and set aside for further processing.

Saponification 0.75 kg of oil/wax phase from the previous batch melt was added to a saponification vessel and heated to 85° C. with continuous agitation. 2.8 kg of a caustic alkali solution having 3% by weight of NaOH and 16% by weight of NaCl, was slowly added to the vessel with continued agitation. Agitation continued after the all of the caustic alkali solution was added and was stopped after a saponified soap mass formed. The saponified soap mass, including the aqueous alkali phase containing the spent lye bulk, was removed from the vessel and was placed in an oven at 85° C. for settling. After settling, the aqueous alkali phase was removed from the saponified soap mass and stored for reuse in future saponification. The saponified soap mass was prepared for fitting.

Fitting 2.5 kg of the saponified soap mass was added to the fitting vessel and heated to 85° C. with continuous agitation. 1.7 kg of a caustic alkali solution having 3% by weight of NaOH and 10% by weight of NaCl, was slowly added to the vessel with continued agitation. Agitation continued after the all of the caustic alkali solution was added and was stopped after boiling was uniform and the soap layer thins. The fitted soap mass, including the aqueous alkali phase was removed from the vessel and was covered to prevent vapor loss and placed in an oven at 85° C. for settling. After settling, the aqueous phase was removed and stored for future reuse.

0.4 kg of the fitted soap mass was placed back in the vessel and re-heated to 85° C. with continuous agitation. 0.07 kg of heated water (85° C.) was added with continued agitation until the fitted soap mass became uniformly fluid. The fitted soap mass was removed from the vessel and was covered and placed in an oven at 85° C. for 3-4 days for settling. After settling, the fitted soap was removed and separated into a neat soap and slurry soap.

What is claimed is:

1. A method comprising:
    (1) melting a solid or semi-solid antiperspirant composition within a package;
    (2) removing the molten antiperspirant composition from the package;
    (3) settling the molten antiperspirant composition directly from steps (1) and (2) for a period of 6 to 72 hours so as to settle the molten composition into a liquid phase having an oil/wax phase, and a solid phase having an antiperspirant active;
    (4) separating the solid phase from the oil/wax phase by washing the melted antiperspirant composition with water to form an aqueous phase in the liquid phase, wherein washing the melted antiperspirant composition distributes the antiperspirant active in the aqueous phase, and washing separates the solid phase from the oil/wax phase within 3 hours; and
    (5) treating the liquid phase to reclaim one or more components thereof, which comprises removing the aqueous phase for reclaiming of the antiperspirant active; and saponifying the oil/wax phase.

2. The method of claim 1, wherein the solid or semi-solid antiperspirant composition is disposed within the package and the package comprises a recyclable material, and the method further comprises:
    removing the antiperspirant composition from the package; and
    recycling the recyclable material of the package.

3. The method of claim 1, wherein melting the solid or semi-solid antiperspirant composition comprises heating the composition at a temperature in a range of 70° C. to 100° C.

4. The method of claim 1, wherein the liquid phase comprises a plant oil, an emollient, and a fatty alcohol.

5. The method of claim 1, wherein the oil/wax phase comprises palm kernel oil, castor wax, behenyl alcohol, stearyl alcohol, and hydrogenated soybean oil.

6. The method of claim 1, wherein the component reclaimed is a neat soap or a spent lye.

7. The method of claim 1, wherein settling the antiperspirant composition into a liquid phase and solid phase occurs within a time period that is in the range of 6 hours to 36 hours.

8. A method comprising:
    (1) melting a solid or semi-solid antiperspirant composition within a package;
    (2) removing the molten antiperspirant composition from the package;
    (3) settling the molten antiperspirant composition directly from steps (1) and (2) for a period of 6 to 72 hours so as to settle the molten composition into a liquid phase having an oil/wax phase, and a solid phase having an antiperspirant active;
    (4) separating the oil/wax phase of a molten solid or semi-solid antiperspirant composition from a solid phase having an antiperspirant active, wherein separating the oil/wax phase from the solid phase comprises washing the antiperspirant composition with water to form a liquid phase comprising an oil/wax phase and an aqueous phase;
    (5) saponifying the oil/wax phase to form a saponified soap mass;
    (6) fitting the saponified soap mass to form a fitted soap mass; and
    (7) separating a neat soap from the fitted soap mass.

9. The method of claim 8, wherein the antiperspirant composition comprises an antiperspirant active, a plant oil, an emollient, and a fatty alcohol.

10. The method of claim 8, wherein the oil/wax phase comprises palm kernel oil, castor wax, behenyl alcohol, stearyl alcohol, and hydrogenated soybean oil.

11. The method of claim 8, wherein saponifying the oil/wax phase comprises:
    heating the oil/wax phase; and
    contacting the oil/wax phase with a caustic alkali solution.

12. The method of claim 11, wherein the caustic alkali solution comprises a solution of sodium hydroxide and sodium chloride, wherein the caustic alkali solution comprises 0.1 to 3 percent by weight of sodium hydroxide and 10 to 21 percent by weight of sodium chloride.

13. The method of claim 11, wherein saponifying the oil/wax phase further comprises continuous agitation of the oil/wax phase during contact with the caustic alkali solution.

14. The method of claim 8, further comprising:
    removing a spent lye component from the saponified soap mass.

15. The method of claim 8, wherein the fitted soap mass further comprises a slurry soap.

16. The method of claim 8, further comprising drying the neat soap.

17. The method of claim 8, wherein the neat soap comprises an anhydrous soap, an alkali salt, an alkali hydroxide, glycerol, and water.

18. The method of claim 17, wherein the neat soap comprises 60% to 72% by weight of the anhydrous soap, 0.5% to 1.5% by weight of sodium chloride, 0.01% to 0.5% by weight of sodium hydroxide, 0.5% to 3% by weight of glycerol, and water.

* * * * *